United States Patent [19]

Collins et al.

[11] Patent Number: 4,681,996
[45] Date of Patent: Jul. 21, 1987

[54] ANALYTICAL PROCESS IN WHICH MATERIALS TO BE ANALYZED ARE DIRECTLY AND INDIRECTLY HEATED AND DRIED BY MICROWAVE RADIATION

[75] Inventors: Michael J. Collins; Wyatt P. Hargett, Jr., both of Matthews, N.C.

[73] Assignee: CEM Corporation, Matthews, N.C.

[21] Appl. No.: 811,540

[22] Filed: Dec. 19, 1985

Related U.S. Application Data

[62] Division of Ser. No. 450,198, Dec. 16, 1982, Pat. No. 4,566,804.

[51] Int. Cl.$^4$ .................. H05B 6/78; G01N 25/00
[52] U.S. Cl. .................. 219/10.55 M; 219/10.55 F; 374/14
[58] Field of Search .................. 219/10.55 F, 10.55 E, 219/10.55 B, 10.55 M, 10.55 R; 99/DIG. 14, 451; 34/1; 374/14

[56] References Cited

U.S. PATENT DOCUMENTS

| | | | |
|---|---|---|---|
| 3,585,258 | 6/1971 | Levinson | 219/10.55 E X |
| 3,662,141 | 5/1972 | Schauer, Jr. | 219/10.55 E |
| 3,890,825 | 6/1975 | Davis | 374/14 |
| 4,266,108 | 5/1981 | Anderson et al. | 219/10.55 E |
| 4,307,277 | 12/1981 | Maeda et al. | 219/10.55 R |
| 4,362,917 | 12/1982 | Freedman et al. | 219/10.55 F |
| 4,441,002 | 4/1984 | Teich et al. | 219/10.55 M |

*Primary Examiner*—Philip H. Leung
*Attorney, Agent, or Firm*—Raymond F. Kramer

[57] ABSTRACT

An apparatus for controllably heating material, such as a material to be analyzed for volatiles or non-volatiles contents, directly and indirectly by microwave radiation, includes a chamber, in which the material to be heated is placed, a source of microwave radiation, for radiating onto materials in the chamber and for controllably heating such a material, and a support for such material, which support includes a matrix of a material which transmits microwave radiation, and also includes particulate material therein which absorbs microwave radiation. The absorptive material is one that has a Curie temperature, above which it is transmissive of microwave radiation, so as thereby to prevent excessive heating of the support and the supported material which is to be heated. The matrix material is stable and form-retaining at the Curie temperature of the dispersed material. Preferably the support matrix will be of a silicone rubber or of a polyfluoroalkylene polymer, such as polytetrafluoroethylene, and the dispersed material will be a ferrite, garnet or a mixture thereof. The apparatus may include a turntable for one or more supports, an automatic electronic balance, computerized controls and readout means. Also within the invention are the described support, and processes for heating and drying, in a preferred embodiment of which processes a particulate diluent or dispersant for the sample being treated is employed to prevent overheating of the sample.

10 Claims, 9 Drawing Figures

ANALYTICAL PROCESS IN WHICH MATERIALS TO BE ANALYZED ARE DIRECTLY AND INDIRECTLY HEATED AND DRIED BY MICROWAVE RADIATION

This is a division of application Ser. No. 450,198, filed Dec. 16, 1982, now U.S. Pat. No. 4,566,804, issued Jan. 28, 1986.

This invention relates to an apparatus for controllably heating materials by means of microwaves. More particularly, it relates to heating a relatively small amount of a material to be dried or from which volatiles are to be removed, with the energy from the microwaves being supplied to the material directly, and indirectly (through a microwave absorptive support). The invention also relates to processes for effecting such heating and to articles (supports for the materials being heated) which are heated by microwave radiation and which transfer their heat to the materials being treated.

Heatings of relatively small quantities of various materials to effect drying, evaporation, chemical reaction and digestion, and for other laboratory and analytical purposes, are carried out routinely. Microwave heating of a wide variety of substances, such as foods, drugs, cosmetics, blood, gels and various other materials containing a lossy dielectric, such as water, have been effected and some such heating methods are in commercial use. The microwave oven is now a common household appliance and microwave heating and cooking of foods is conventional in some restaurants and in many homes. In recent years microwave heating, drying, digestion and moisture analyses of a wide variety of materials, including dairy products, chemicals, foods, pulp and paper products, pharmaceuticals and cosmetics, to name only a few, have been quickly and accurately effected by means of commercially available apparatuses, e.g., the AVC-80 TM Moisture/Solids Analyzer, the AVC-MP TM Automatic Volatility Computer, and the MDS-81 TM Microwave Drying/Digestion System, all manufactured by CEM Corporation.

Although microwave heatings of various materials have been known they have depended on the presence of moisture in the material to be heated. Thus, if there is little or no moisture (or other lossy dielectric) present in the sample heating will not take place. When analyzing for moisture content an apparatus incorporating a microprocessor digital computer (such as the AVC-MP and the AVC-80) can monitor the drying curve (weight loss v. time) and can predict the final dry weight (or moisture content) based on an initial portion of the drying curve. Such analyses usually may be conducted in about two to three minutes. However, when a programmable analyzer or a microprocessor digital computer is not available or when more complete drying is desired in a short time than would otherwise be available with conventional microwave heating of a sample, the present invention is particularly advantageous (although it has many other uses too). By means of this invention the sample to be heated may be initially or substantially dried (or volatiles may be removed from it) by direct microwave radiation onto the sample and it may be indirectly heated, often to an anhydrous or volatiles-free state, faster and/or to a greater extent than would be obtainable by direct microwave heating, by heating of a support for the sample, and indirect heating of the sample by the support.

This is an important advance, especially in the art of analyzing for volatiles, such as moisture, in products of relatively low moisture contents. Because some or all of the moisture present in low moisture content materials, such as tobacco, dried milk powder, and detergents tends to be strongly held or bound or for other reasons resists removal by microwave radiation, other microwave analytical devices often were most useful for employment only with higher moisture content materials. Now, however, the present apparatus allows the accurate drying and analysis of materials of relatively low volatiles contents, too. In such cases, the thermal heating of the specimen or sample by the support releases the crystalline water from the sample, and that water is then vaporized by the microwave radiation. A truly synergistic effect is obtained because the thermally heating support does not have heat extracted from it to heat free water and the heat in the support can then heat and "release" more hydrate, crystal, or otherwise tightly bound or "non-polar" water, which will be vaporized by microwave radiation, which process is then repeated. Also, when non-polar solvents are present with bound or free water in a material to be analyzed for volatiles, as is often the case, they are volatilized by the thermal heat from the support, while free water, which may have been freed from a bound form, is vaporized by the microwave radiation. Thus, volatiles are removed from the test sample to be dried (often for analytical purposes) and such removal is effected quickly, whether or not the volatiles are bound water, free water, other polar materials or non-polar compounds. A further advantage obtained is that moisture present in the test specimen with any non-polar volatile material helps to sweep out the volatile compounds as such moisture is vaporized, even helping to remove small droplets thereof which then may be vaporized by the heat of the water vapor and any accompanying air stream (generated by an exhaust fan).

In accordance with the present invention, an apparatus for controllably heating a material directly and indirectly by microwave radiation comprises a chamber, a source of microwave radiation for radiating onto materials in such chamber for controllably heating such material, and a support for such material, which support comprises a matrix material which is transmissive of microwave radiation, with a microwave absorptive material dispersed in such matrix material, which microwave absorptive material has a Curie temperature, above which it becomes microwave transmissive, so as thereby to prevent excessive heating of the support and the material thereon which is to be controllably heated, which matrix material is stable and form-retaining at the Curie temperature of the dispersed material. Among the apparatuses within the invention are those intended for heating, which may include a suitable turntable device to allow for the heating of several samples simultaneously, and analyzers, including weighing means, such as an electronic balance, and preferably also incorporating a microprocessor digital computer. Also within the invention are processes for controllably heating and/or analyzing, and supports for the sample which can heat it even after it no longer contains enough lossy dielectric, such as water, to cause it to absorb microwave energy. In one such process a thermally sensitive material is analyzed for its content of volatilizable components without degrading such material due to heating it to release more than the volatilizable components therefrom, by heating the material to be analyzed by microwave radiation, directly and indirectly. Such process comprises supporting the material to be analyzed by means of a support which comprises a matrix material which is transmissive of microwave radiation, and which has dispersed in such matrix material a particulate microwave absorptive material, which microwave absorptive material has a Curie temperature in the range of 85° to 650° C., above which it becomes microwave transmissive, so as thereby to prevent excessive heating of the support and the material being analyzed, which matrix material is stable and form retaining at the Curie temperature of the dispersed material therein, and directing microwave radiation onto the material to be analyzed and onto the support therefor, so as to heat the material directly and to heat it indirectly by heating the support, which heats the material being analyzed, and applying sufficient microwave radiation to the support to bring the support to the Curie temperature of the dispersed microwave absorptive particulate material therein.

A search of the art which was performed in the United States Patent and Trademark Office in Subclasses 73-73; -74; -75; -76; 177-1; -245; 219-10.55; -10.67; -508-519 (scanned); 252-62.54; -62.56; 364-567; 423-594; and 426-241; and -242, resulted in the finding of the following patents which are considered of relevance: U.S. Pat. Nos. 2,830,162; 3,027,327; 3,936,626; 3,949,184; 4,154,855; 4,264,361; 4,266,108; 4,276,462; 4,283,427; and 4,308,155. Also of interest are U.S. Pat. Nos. 3,909,598 and 4,291,775, in both of which one of the present inventors is an inventor, and a text entitled *Microwave Heating*, by David A. Copson, published by AVI Publishing Co., Inc., which, at pages 283–285, mentions that ferrites intrinsically control temperatures. Also, prior to the present invention ferrite ceramic discs had been employed by the present inventors in an effort to heat samples of materials by microwave radiation and thermally, but although useful heatings could be obtained with such discs in specific instances, the discs were not sufficiently stable to be commercially feasible and in many cases, despite the fact that the ferrites employed had Curie temperatures, "runaway" conditions resulted and samples being heated and/or analyzed were excessively heated, which often caused degradation and incorrect analytical results. Various publications and patent applications which may also be relevant to the present invention describe components of the invention, apparatuses and/or processes. These will be mentioned later in this specification, and are incorporated by reference herein, as are the foregoing two patents, U.S. Pat. Nos. 3,909,598 and 4,291,775.

Of the search patents listed above it is considered that the most relevant are U.S. Pat. Nos. 4,266,108, 4,264,361 and 4,308,155. The first of these patents describes a microwave heating device in which a microwave reflecting member is positioned adjacent to a microwave absorbing material having a Curie temperature. The patent teaches that the microwave absorbing material may be a ferrite and the patent describes utilization of the ferrite as a support and as a switch to limit the temperature of food being cooked or browned (to prevent burning). Also of interest are the citations given in the patent at columns 1 and 2 thereof. The '361 patent discloses magnets containing ferrites in a rubber that contains a particular type of siloxane. U.S. Pat. No. 4,308,155 describes the making of magnets wherein a magnetic powder, such as a ferrite, is dispersed in a plastic or rubber. Included in a list of various rubbers which may be employed is silicone rubber and among the plastics "fluoroplastics" are listed. This patent is directed only to the manufacture of magnets and powders which may be incorporated in such magnets, and does not mention microwave heating or drying of materials.

The prior art noted, which is the closest prior art known to applicants, does not disclose their invention and does not make it obvious, alone or in any combination thereof.

The invention, in its various aspects, will be readily understood from the present specification and the following description of some embodiments thereof, taken in conjunction with the drawing, in which.

Figure 1:
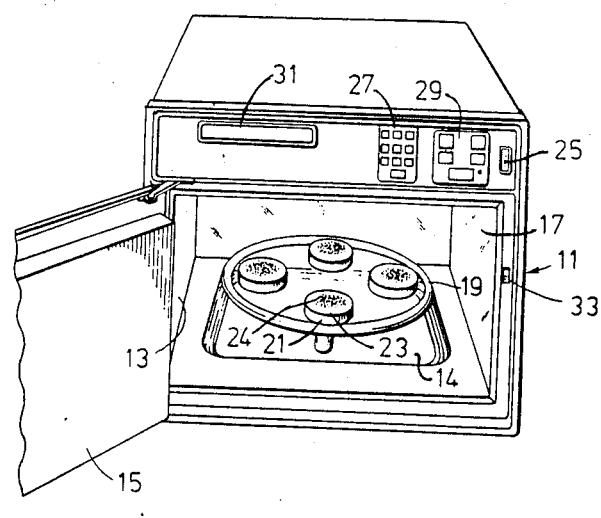
FIG. 1 is a perspective front view of an apparatus of this invention (including a turntable) for the microwave and thermal drying of materials.

In FIG. 1 microwave drying apparatus 11 includes internal walls like that represented by numeral 13, a bottom 14 and a door 15, defining a chamber 17, in which there is mounted a turntable 19, which is shown carrying, in substantially uniformly spaced disposition, four microwave absorptive supports 21, each of which has on top of it a disposable fiberglass pad or equivalent heat resistant, microwave transmissive (microwave transparent) pad 23 and sample or material 24 to be heated or dried. The surface of turntable 19, on which supports 21 rest, is preferably perforated or screenlike to allow for heat to be dissipated from the support and to prevent overheating of such surface. At least the part of the turntable (or other part on which the invented support(s) rest) under the support(s) should be open to prevent overheating due to there being no lower outlet for the thermal heat generated in the support. A preferred supporting surface is of Teflon or other PTFE covered glass fiber screening, which will usually be from 0.5 to 2 mm. thick, e.g., 1 mm., with appropriate openings, as in a No. 10 to No. 50 screen (U.S. Sieve Series). Instead of a plurality of supports a single support may be used, covering a screen turntable 19, or such turntable may be made of the material of the microwave heatable support. In addition to use with the apparatus equipped with a turntable the single larger (and thinner) support and the glass screen (preferably covered with PTFE) may also be used in the AVC-80 and other microwave heating and analyzing apparatuses.

Means, not illustrated, are provided for rotating the turntable, and preferably such rotation will be at any of a plurality of suitable different speeds. The microwave apparatus includes a microwave generator, not shown (but positioned between inner and outer walls of the apparatus), which may be like that in the CEM Corporation MDS-81 Microwave Drying/Digestion System, or another suitable magnetron or equivalent microwave generator may be employed. Such will very preferably generate focussed microwave radiation, concentrated or directed at the level of the supports and the material(s) to be heated. Because the microwave radiation is substantially evenly delivered to the material to be heated sometimes the turntable may be replaced by a stationary supporting platform, screen or other holder. However, for most even radiation onto the material use of the turntable is preferable. The illustrated preferred microwave apparatus also includes an on-off switch 25, a programmable microprocessor digital computer which is capable of programming a plurality of microwave radiation powers to be applied over a plurality of sequential time periods, not shown, controls 27 and 29 for such microprocessor, a readout screen 31, an exhaust fan, not illustrated, which is preferably of controllably variable speed, and a door latch 33.

Figure 2:
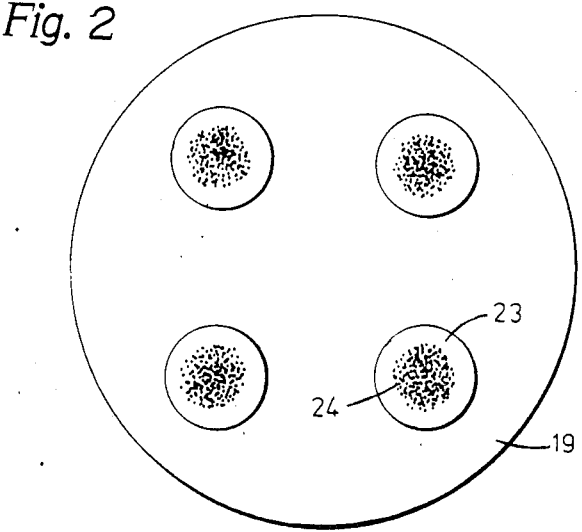
FIG. 2 is a top plan view of the turntable of FIG. 1, showing the positioning of four microwave-heated supports for materials to be heated.

In FIG. 2, an enlarged top plan view of the turntable of FIG. 1, with supports, pads and samples thereon, pad 23 conceals support 21, not shown in FIG. 2. However, in some embodiments of the invention it may be desirable to utilize the microwave heatable supports 21 without intervening pads 23. Also, other types of supporting members which may be of different shapes, may be substituted for supports 21, and pads 23 may be similarly replaced.

Figure 3:
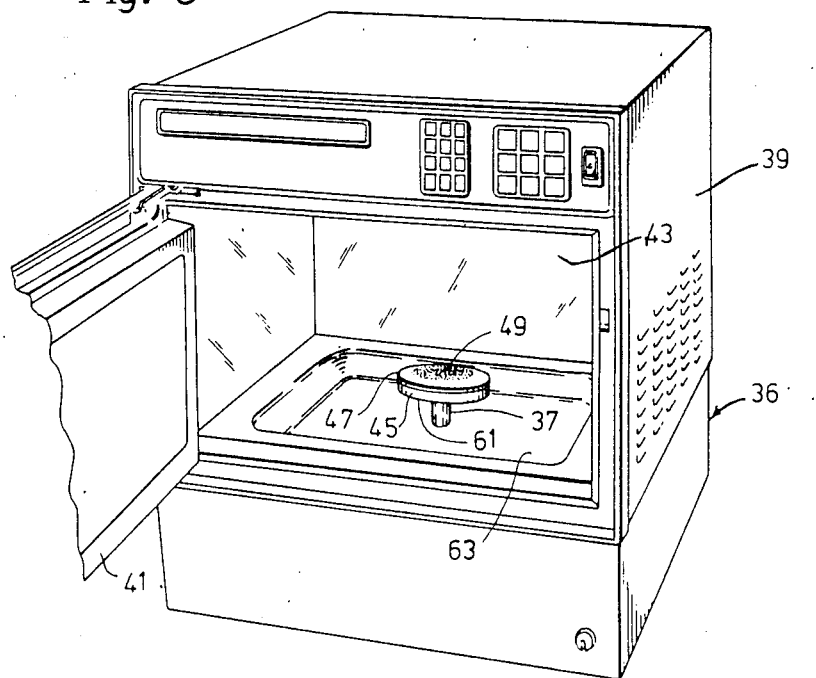
FIG. 3 is a front perspective view of another apparatus of this invention, which incorporates weighing means for determination of the weight of the sample from which volatile material has been removed by a combination of microwave and thermal heating.

FIG. 3 illustrates heating and weighing apparatus 36 much like that of FIG. 1, but also containing weighing means 37 instead of turntable 19. In housing 39, the interior of which, with door 41, defines a chamber 43, weighing means 37, which is shown in greater detail in FIG. 4, has thereon a support 45, a pad 47 and material 49 to be heated and analyzed. The apparatus also includes a switch, controls and a readout function like those shown in FIG. 1, with some modifications. Additionally it includes means, not shown, for generating a focussed microwave beam directed at about the level of the support and sample, an exhaust fan, not shown, and a door latch.

Figure 4:
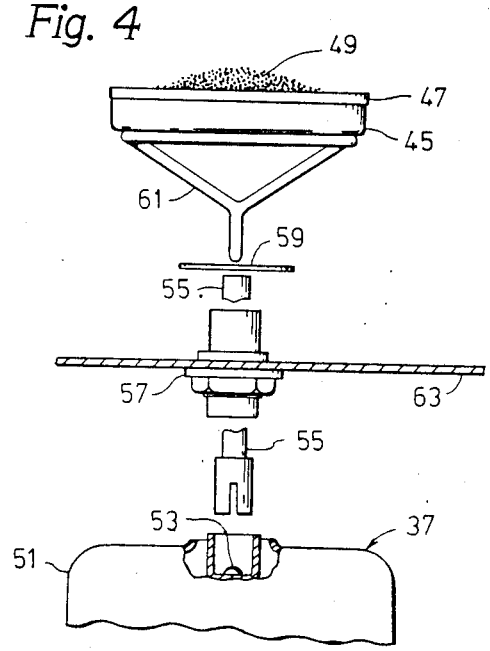
FIG. 4 is a partially sectioned, partial, disassembled view of the weighing means of FIG. 3, including sample supporting means.

In FIG. 4 are shown various parts of the weighing means 37, with the support, pad and material thereon. A balance module 51 includes means, represented by numeral 53, responsive to weights applied thereto, balance stem 55, stub bushing means 57, a fiber washer 59, and a balance pan 61. Numeral 63 represents the floor of the apparatus of FIG. 3, through which the balance stem moves in response to changes of weights thereon. In another embodiment of the invention, not specifically illustrated, balance pan 61 may be made of the material of support 45, and material 49, which is to be heated, may be placed directly in contact with such balance pan of microwave absorptive material (or containing such material), but such direct contact is often less desirable.

Figure 5:
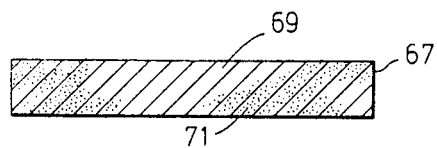
FIG. 5 is a central vertical sectional view of a support of this invention, which comprises a microwave absorptive particulate material dispersed in a heat resistant elastomeric or polymeric plastic matrix.

In FIG. 5 disc-shaped support 67 includes a matrix 69 of microwave transmissive, heat stable elastomer or polymeric plastic or equivalent material and a microwave absorptive spinel, preferably a ferrite, synthetic garnet, mixture thereof, or equivalent 71, having a Curie temperature above which it becomes microwave transmissive, thereby providing a "safety switch" to prevent overheating of the support and any material in contact with it. Although the flat circular shape of the support is preferred, various other shapes may also be utilized and, as will be apparent from FIG. 7, supports may be made by coating bases of microwave transmissive materials with microwave absorptive mixtures.

Figure 6:
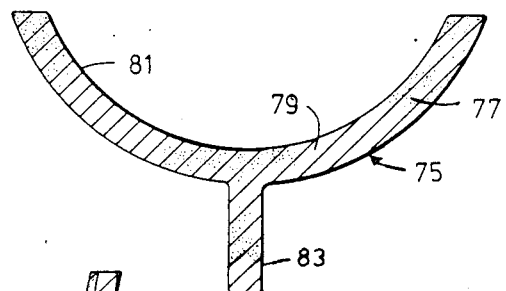
FIG. 6 is a central vertical sectional view of an alternative form of support of this invention, in the form of a balance pan.

FIG. 6 shows a generally circular balance pan, suitable for use with the apparatus of FIG. 3, which is made of the same composition as (or equivalent to) that of the support of FIG. 5. Like the flat circular support, the balance pan 75, with its garnet or ferrite particles 77 distributed throughout matrix 79 of silicone rubber or similar heat resistant and microwave transmissive material may have resting on it a fiberglass or similar pad, which can be curved to fit the shape of receptacle portion 81 of the balance pan, with material to be heated being placed on top of the pad. Extension 83, for fitting to the balance stem, may be of the same material as the rest of the balance pan, as illustrated, or may be made so as to contain no garnet, ferrite or microwave-absorptive particulate material.

Figure 7:
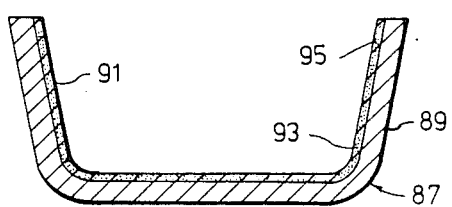
FIG. 7 is a central vertical sectional view of another embodiment of a support of this invention.

In FIG. 7 there is illustrated a microwave absorptive support 87 in the form an evaporating dish in which material to be heated in apparatuses of this invention may be placed. Support 87 comprises an external body portion 89 and an internal portion 91 which is in the form of a coating on the interior of the dish body. Body 89 is of a material which is not microwave absorptive and coating 91 comprises a matrix 93 of similar microwave transmissive material and, substantially evenly distributed throughout such coating, particles 95 of microwave absorptive material. For example, the microwave transmissive material may be a room temperature vulcanized silicone rubber or polytetrafluoroethylene, and the microwave absorptive particles may be suitable garnets, ferrites or mixtures thereof. While it is usually preferable for the coating matrix to be of the same material as the dish body it is within the invention to utilize different materials, providing that the coatings satisfactorily hold to the bodies during normal use. Instead of adding the material to be heated to the illustrated evaporating dish type of receptacle or support, so that it is in contact with the coating therein, an intermediate pad, such as previously described, which may be shaped to conform to the contours of the dish, may be utilized. In some cases, so as to promote additional thermal heating of the material being treated, microwave absorptive particles or fibrous materials containing such particles adhered to or distributed within them may be incorporated in the pad, preferably with a suitable microwave transmissive matrix type material also being present (which may be useful as a binder).

Figure 8:
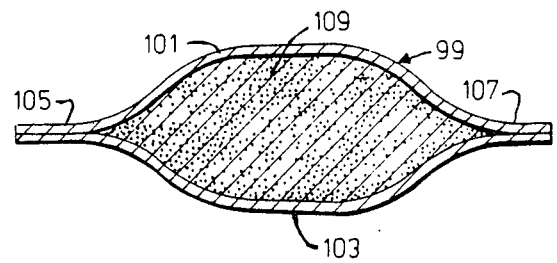
FIG. 8 is a sectional view of yet another embodiment of a support.

In FIG. 8 support 99, which is generally circular in shape but may be of rectangular "pillow" shape, includes two walls 101 and 103 of microwave transmissive material joined together at ends 105 and 107, by any suitable means (high temperature heating sealing, chemical reaction and heat resistant adhesive sealing being preferred) so as to enclose heat absorptive particles 109. The heat absorptive particles may be mobile within the support or packet 99 and may have an inert particulate dispersant (not illustrated), such as sand, mixed with them to modify the heat absorbing characteristics of the particles (which preferably will be garnets and/or ferrites). Also, other microwave transmissive materials, such as polymeric plastics or elastomers, e.g., silicone rubber particles, may be present. If desired, the microwave absorptive particles and/or dispersant may be bound in a vulcanized or cured matrix of elastomer, such as silicone rubber, or polymer, such as polytetrafluoroethylene, and films 101 and 103 may be employed as covers for such cured support.

Figure 9:
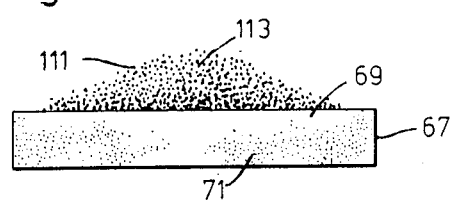
FIG. 9 is an enlarged representation of a portion of a support of this invention with a covering pad thereon and, on the pad, a mixture of material to be heated and dispersant material.

In FIG. 9 there is shown the support of FIG. 5 with a mixture of a material to be heated and dehydrated (or to have other volatiles than water removed from it) mixed with a dispersant or diluent material in particulate form, which dispersant helps to prevent overheating of thermally sensitive samples by the microwave radiation of apparatuses like those of FIGS. 1 and 3. Thus, defatted milk powder particles 111 are shown dispersed in about 1.4 times (by weight) of particles of salt (NaCl), quartz or sand 113, which are preferably of about the same particle size. It is found that when support 67 and the mixture of sample material and dispersant are subjected to microwave radiation, the support is heated and initially comparatively easily removable moisture is volatilized off from the sample. Subsequent to the removal of such moisture the sample material is no longer readily heated by the microwave radiation but moisture in it may be volatilized off by thermal transfer of heat from support 67. The presence of dispersant 113 minimizes any overheating of the sample and prevents deterioration thereof. Thus, the sample is heated to dryness, with normally difficultly removable moisture (or other volatiles) being driven off, without damage to the remaining components of the sample. Such removal of volatiles is speedier than that of conventional treatments, and the described method allows complete removal of the volatiles, which is difficult to effect by utilization of microwave radiation of the sample alone.

The apparatuses for the application of microwave energy to materials to be heated, dried and/or analyzed may be any such suitable microwave apparatuses which can direct microwave radiation onto the contained sample or material to be treated. Household microwave ovens are not usually satisfactory but they may be useful in some instances. Preferably, the apparatus will incorporate a microprocessor digital computer and controls for regulating the application of microwave radiation to the material to be treated, such that different levels of radiation or powers, preferably higher initially and lower later in the process, may be applied for different time periods. For example, three different levels of microwave radiation may be applied, over three different time periods, which levels and time periods may be individually set. It is also preferred for the microwave apparatus to include readout means, especially for automatic analyzers, so that the progress of the analysis may be followed. In other cases, treatment conditions may be monitored by reference to the readout screen.

Preferred microwave apparatuses which may serve as the basic apparatus structure, to be completed by additions of support, pad and material to be treated, are the AVC Automatic Volatility Computer (preferably AVC-MP), the AVC-80 Moisture/Solids Analyzer and the MDS-81 Microwave Drying/Digestion System, all made by CEM Corporation. Such are described: in operation and service manuals entitled Automatic Volatility Computer AVC ™, and Automatic Volatility Computer Model AVC ™-MP, published in 1975 and 1979, respectively, by CEM Corporation, and in an article entitled Moisture/Solids Control Using a New Analytical Technique, by Dr. M. J. Collins, one of the present inventors, published in American Dairy Review, May, 1979; in a brochure entitled CEM Corporation Moisture/Solids Analyzer, AVC-80, published in 1981; and in a brochure entitled CEM Corporation Microwave Drying/Digestion System, MDS-81, Laboratory Microwave System, published in 1981. The CEM Corporation publications contain specifications for such equipment. All five publications are incorporated herein by reference.

It is noted that in the apparatuses mentioned the microwave power range is from 0 to 100% of full power (600 watts) in 1% increments. Of course, greater powers can also be employed, for example up to several kilowatts, but such are usually unnecessary. In the United States the frequency of microwave radiation employed will normally be 2.45 gigahertz whereas in Great Britain it is 0.896 gigahertz. However, such frequency can be in the ranges from 0.8 to 3 gigahertz or 0.3 to 50 gigahertz and even higher. The readouts of the described apparatuses have as many as 40 character alphanumeric displays and in some instances include an audible tone for operator feedback. The operator controls include a keyboard with up to 21 keys for input. In the case of the electronic balance the sensitivities are approximately one part in 40,000 over a range from 5 grams to 100 grams, and products containing from 0.1 to 99.9% of water or other lossy dielectric or microwave absorbing material may be treated to remove such material.

In addition to the publications mentioned such apparatuses are described in U.S. Pat. Nos. 3,909,598 and 4,291,775, and also in U.S. patent applications Ser. Nos. 06/21,986 for Analytical Method and Apparatus now abandoned; 29,882 for Method and Apparatus for Improving Weighing Accuracy (Collins et al.) U.S. Pat. No. 4,457,632; and Ser. No. 05/603,354 for Automatic Volatility Computer, now abandoned, all of which are also incorporated herein by reference.

Although various polymeric and elastomeric materials are useful as the matrix material or a base material for coating with a matrix-ferrite type of lining, since most such materials are microwave transparent and are not heated by the application of microwaves, the preferred, and sometimes critically preferred materials that are employed are silicone rubbers and polyfluoroalkylenes. Thus, although nylons, dacrons, polypropylenes, polyvinyl chlorides, phenol formaldehydes, polyacetals, polyesters, polyethers, neoprenes, polycarbonates, polymethylpentenes, ABS polymers and polystyrene may be employed as matrices or components of matrices in various instances (sometimes mixtures thereof may be used), normally the materials of choice will be silicone rubbers, preferably room temperature vulcanized silicone rubbers, and polyfluoro-lower alkylenes, wherein the lower alkylenes are ethylene and/or propylene and/or mixtures thereof.

It is preferred that the polyfluoroalkylenes be highly fluorinated and that fluorine be the only halogen present but polychlorofluoroalkylenes may also be utilized in some instances and in some cases polybromofluoroalkylenes may be employed. Preferred polyfluoroalkylenes are those of ethylene and propylene or mixtures thereof and most preferably, a polyperfluoroalkylene, such as polytetrafluoroethylene, will be utilized. Such types of products are sold under the trademark Teflon ® and are known as TFE and FEP. They are available in various forms, including molding powders, under the Teflon, Kel-F, Aclar, Halon and Fluorel trademarks. Although the polyfluoroalkylene polymers are thermoplastic they may be useful up to temperatures of about 285° C., and even higher. For a review of suitable polytetrafluoroethylenes also see Encyclopedia of Polymer Science and Technology, Volume 13, pages 623–654.

The silicone rubbers are organosiloxane polymers which are preferably formed from methylchlorosilanes which are hydrolyzed and polymerized in known manner. They are stable at temperatures up to over 250° C., e.g. 300° C. and are water repellant, which are advantages for the present applications. Instead of the elastomers, which may be made by room temperature curing, as with a known curing agent, such as that sold under the trademark RTV by the General Electric Company (which may be used in conjunction with RTV silicone rubber compounds, made by the same company), other silicone polymers, which have the same high temperature resistant (and preferably also the moisture repellant) characteristics, may also be utilized, even though they are not elastomeric. Still, it has been found that the silicone elastomers are highly preferred. They transmit internally generated heat well, conform to different surfaces, are easily compounded with ferrite and garnet powders and cooperate with such materials of various types to prevent runaway heatings. The manufacture and properties of such materials are described in Encyclopedia of Polymer Science and Technology, Volume 12, pages 464–569 (Interscience Publishers New York, N.Y., 1970). Both the encyclopedia sections referred to are incorporated herein by reference.

The microwave absorptive materials having a Curie temperature, which limits the heating of such materials by microwaves and prevents runaway conditions, at which temperatures are increased beyond allowable limits, are preferably ceramic ferrites and garnets but mixtures of such materials can also be employed. Mixtures may be desirable to slow the rate of heating as the Curie temperature of one of the components is passed. Ferrites or ceramic ferrites are well known materials and oxide ferrites have been employed in automatic control systems and in conjunction with microwave ovens and radar systems. It has been found that ceramic ferrites in the forms of baked discs, etc., may be ground to suitable particle size and then incorporated into the polymeric matrix. Synthetic garnets are also well known and certain of the garnets have been employed in microwave devices. Ferrites or ferrospinels and applications thereof are described in *Ferrites, a Review of Materials and Applications* by E. E. Riches, published by Mills and Boon, London (1972) and the properties of ferrites and garnets are described in a bulletin entitled Trans-Tech Microwave Materials, issued by Trans-Tech, Inc. in November, 1980, at sheets 1 and 2 (of 4) thereof. The ferrites are also described in Bulletin No. 651, issued by the same company, entitled Ferrite Basic Theory, a Review of Physical Properties of Ferrites, at page 1 thereof. Such publications are incorporated in this specification by reference.

The mentioned Trans-Tech publications list other bulletins issued by Trans-Tech Inc., which are also incorporated herein by reference, especially Bulletins 120-67 for nickel ferrite, identified by code TT2-111; 264-76 for lithium ferrite, identified by TT72-3000; 151-67, for yttrium garnet, identified by G-113; and 160-67 for aluminum doped garnet, identified by G-1210.

The microwave absorptive spinels (or ferrites) and garnets or any suitable mixtures thereof may initially be in plate, disc or other comparative large solid form, or in particulate form but in the present invention the particulate or powdered form is employed. The particle sizes of the ferrite and/or garnet will normally be in the range of Nos. 10 to 325 sieves, U.S. Sieve Series, preferably 60 to 200 and more preferably, 120 to 180. Particles in such ranges may be obtained by suitable size classifications of powders or particulate mixtures in which size distributions are wider, or may be obtained by crushing ceramic discs or other larger forms of the absorbers, such as discs of nickel or lithium ferrites, and sieving the resulting particles. Within the described particle size ranges the microwave absorbers are comparatively easily handleable, and when they are distributed throughout a suitable matrix they facilitate the making of a support of uniform heating characteristics, which will not be subject to thermal "runaway". Such result is unexpected, especially in the cases of ferrites having dielectric loss tangents greater than 0.0002, such as nickel ferrites and lithium ferrites, e.g., TT2-111 and TT72-3000, because such materials, when in ceramic plate form, may be subject to runaway and can be heated by microwaves to above their Curie temperatures. The dielectric loss tangent should be less than 0.0002 when ceramic spinel discs or plates are employed to avoid thermal runaway but spinels of higher dielectric loss tangents may be employed when they are in particulate form and distributed through a microwave transmissive polymeric matrix, in accordance with this invention. The dielectric loss tangent for both spinels and garnets employed in this invention will usually be less than 0.003 and will preferably be less than 0.001. When garnets are used such DLT will generally be less than 0.0002.

The microwave absorptive material employed should also be of suitable Curie temperature and saturation magnetization. The Curie temperature at which the microwave absorptive material becomes microwave transmissive, and is no longer heated by microwave radiation, will normally be in the range of about 85° to 650° C., preferably being from 105° to 500° C., more preferably being from 120° to 500° C. in many instances and 120° to 400° C. in other cases. Using such Curie temperatures will usually allow control of the temperature of a specimen being heated to be in the range of 60° to 500° C., preferably 100° to 200° C., e.g., 100° C., 105° C. and 120° C. Generally, it is desirable for the Curie temperature to be lower than the fusion or decomposition temperature of the matrix material but this is not always necessary because the temperature of the matrix material can be controlled by varying the proportions of the matrix and the microwave absorptive powder. Still, it is often desirable to utilize absorptive particles with Curie temperatures below the temperature limits for the matrix material and in such instances the permissible range of Curie temperatures may be from 85° to 300° or 400° C. When water is to be removed from a material directly by radiation and indirectly and thermally by means of a support of this invention a lower limit of 105° C. or 120° C., or even 150° or 200° C. or thereabout may be imposed to make sure that the temperature of the support is high enough so that such water will be removable.

The rate of heating of the spinel or garnet or other microwave absorptive material of this type is directly proportional to the saturation magnetization thereof. Such ranges from about 500 to 5,000 gauss for spinels and from about 175 to 2,000 gauss for garnets. From these figures it is seen that the spinels heat faster. Also, as a rule, they have higher Curie temperatures, although there are many exceptions to such generalizations. Thus, the microwave absorbers will be chosen to provide the desired heating rate and preserve the matrix against decomposition. Such characteristics can be modified by mixing different microwave absorbers and by varying the proportion of absorber in matrix. Also, different sections of the matrix may include one type of microwave absorber and other sections may include another type, so that different heating effects are obtainable. Alternatively, the absorbers may be mixed together so that the limiting upper temperature of the support may be at least somewhat varied during the heating process, to permit control of the rate of heating of the support, as the Curie temperature of microwave absorptive material is surpassed while another or several absorptive materials are still below their Curie temperatures. Such variations of absorptive materials may be employed in conjunction with changes of microwave power over different cycles, to permit closely controlled heating of the sample being treated. In a similar manner different spinels and garnets may be selected with respect to their saturation magnetizations so that the rates of heating may also be controlled. Heating of the sample being treated is also controllable by varying the thickness of the support, which also influences the cooling rate. In practice it has been found practicable to make several types of supports, to raise the sample temperature to different temperatures, e.g., "low temperature" or 100° C. for removal of loosely bound volatiles, especially water, and "high temperature" or 120° C. for removing tightly bound water, e.g., water of hydration in detergent composition builder salts.

The proportions of different spinels and garnets utilized may be any that are considered suitable for particular purposes, control of the effective Curie temperature and/or heating rate(s). Thus, when two or more microwave absorptives are present the proportions may be from 1:99 to 99:1 but normally they are within the range of 1:10 to 10:1 or 1:5 to 5:1. The percentages of total microwave absorptive(s) to matrix material in the support will normally be from 40 to 95% of the matrix and 5 to 60% of the absorptive. Preferably these percentages will be 50 to 90 or 95% and 5 or 10 to 50%, respectively. Sometimes they will preferably be 80 to 95% and 5 to 20%.

Often no extender, diluent or modifier material will be present with the polymeric matrix and the microwave absorptive particles, but such materials can be employed. Among them are quartz, sand and glass but various other polymeric substances may also be useful providing that they are not microwave absorptive (or if they do absorb microwave radiation and emit heat, such absorption effect should be limited and ascertainable so that it does not interfere with analyses for volatiles. The proportion of extender will usually be in the range of 0 to 50%, preferably 5 to 25%, if present.

The supports made will preferably be in circular form but one of the advantages of the invention, especially when the polymer or elastomer may readily be cut, as with a knife, scissors or a suitable die, is that the material of the support can be made in strips or other shapes and may then be cut to final desired shape. Sometimes it may also be pressed to form after manufacture. Although various thicknesses of the supports may be made, usually the thickness should be in the range of 0.5 to 10 mm., preferably 0.5 to 6 mm., and most preferably about 0.5 to 3 mm., e.g., 1 mm., 2 mm. The supports, comprising a solidified matrix containing the microwave absorptive particles, may be made by mixing the particles into the matrix material and solidifying the matrix about them in desired shape, usually by chemical or heat curing, although such may also be effected by cooling thermoplastics (the melting points of which should be sufficiently high to be operative under normal conditions of use of the supports).

As was mentioned in discussing FIGS. 6-8, in addition to utilizing flat discs in which ferrites and/or garnets are substantially uniformly distributed throughout the matrix material, the support may be suitably shaped for particular applications (as in FIG. 6). Also, a coating or lining of the absorptive-matrix composite may be applied to another material, preferably of the same type as the matrix. It will generally be preferred for the body portion of such a support, which may be in the form of an evaporating dish or other container or holder, to be of a thickness in the range of 0.5 to 3 mm., with the coating also being of a thickness in such range. For example, an evaporating dish, made of TFE, may be 2 mm. thick and have on it a coating of garnet in TFE 1 mm. in thickness. Another less preferred microwave heatable support is one wherein the described particles of ferrite or garnet or other suitable microwave absorptive material are dispersed in a matrix of particles of a microwave non-transmissive material, with the particulate mixture being contained in an envelope or other suitable container. The proportions of the microwave absorptive and matrix or diluent in such case will be in the ranges previously given for the molded or formed articles. The envelope may be of any suitable heat resistant material, e.g., TFE, FEP or silicone rubber sheet, the thickness of which will normally be from about 0.1 mm. to 2 mm. The particle sizes of the material will also be in the same ranges. As was previously mentioned, although supports like that shown in FIG. 8 may be operative and useful they are not as good as those embodiments of this invention in which the microwave absorptive particles are dispersed in a continuous matrix.

The supports of this invention may be made by suitable conventional means. Thus, the molded or formed supports may be made by mixing a curable monomer or oligomer with the absorptive particles and curing them in normal manner, so that the particles are fixed in dispersed positions. Alternatively, providing that the melting point is high enough, the absorptive particles may be dispersed in a melted thermopolymer, which is then cooled in such manner as to maintain the particles dispersed. Instead of liquid forms of matrix materials being employed solids thereof may be milled or otherwise mixed with the particles. After mixing the product may be shaped and cured or solidified further. Coatings may be applied as sheet liners that are fastened to a substrate or may be sprayed onto or painted onto substrate walls. Alternative methods of coating may also be used as long as they apply a stable coating to the substrate and as long as both the coating applied and substrate are stable and useful under normal sample treatment conditions.

Although the sample to be treated may be placed directly in contact with the support, and such method has been employed, it is frequently preferable to utilize an intervening material to prevent direct contact of the sample with the support and yet to allow thermal heating of the sample. Among the preferred materials is a non-woven fiberglass of the type which is also useful as a filter. Woven glass products of similar properties may also be utilized and sometimes may be preferred. The fiberglass mat will generally be of a thickness in the range of 0.5 to 2 mm. and preferably will be in the range 0.7 to 1 or 1.5 mm. The individual fibers thereof will usually be very small, often less than 0.1 mm. in diameter, e.g., 0.05 mm.

In carrying out the process of this invention, wherein the material is heated directly and indirectly by microwave radiation such radiation is directed onto the material to be heated (and/or analyzed) and onto the support so that it directly heats the material, directly heats the support and indirectly heats the material with heat in the support. The frequency of the radiation and the power were previously described in conjunction with the descriptions of suitable microwave generating apparatuses such as the AVC, AVC-MS, AVC-80 and MDS-81. During the heating operation the temperature to which the support may be raised is limited by the Curie temperature of the microwave absorptive particulate material in the matrix and when sufficient microwave radiation is applied to the support it brings the absorptive material to its Curie temperature, at which absorption of radiation and consequent heating of the support is significantly diminished or stopped entirely, preferably the latter. To speed up the operation the support will often be preheated but in such cases an intervening pad will normally be employed. While it is possible to have the material being treated resting directly on the support this will usually be avoided when the support is preheated, and also to prevent any adverse reactions with the support. Normally, a pad, such as was previously described, will be placed between the support and the material treated. This will have several desirable effects, protecting the surface of the support, inhibiting any possible localized overheating of the material being treated, and allowing for ready disposal of the sample and reuse of a support without special cleaning. When the invented process is applied to a material which contains a lossy dielectric, such as water, and which is to be controllably heated, at least a major proportion of the lossy dielectric will be removed by direct microwave heating of such material and additional water, usually all the water remaining in the sample, will be removed by thermal heating of the sample by the microwave-heated support, preferably through the intermediate fiberglass pad or mat which rests on the support. The same process is applicable when a coated support, such as an evaporating dish, is employed as the supporting material. Thus, the major proportion of the lossy dielectric is removed by direct microwave radiation, but after such removal the sample becomes transmissive of microwave radiation and it is difficult to remove any additional lossy dielectric, such as any tightly held water of hydration, which is still present. Such can be removed by thermal heating and this is accomplished by absorption of the microwave radiation by the support, and transmission of heat to the sample from the support. When the water of hydration is released by the thermal heat transmitted to the sample by the support it is quickly vaporized by the microwave radiation. The support is prevented from being heated excessively by the Curie effect and when it is raised to its Curie temperature the matrix material is still stable. To better control the process, heating periods, microwave power and microwave absorption may be controlled as previously described, usually in such manner that initial heating is at a greater rate than subsequent heating.

In preferred embodiments of the invention, useful to remove water of hydration and other strongly held water or lossy dielectric from samples after the removal of less tightly bound lossy dielectric or water, the support will often be of such composition as to produce a desired limiting temperature, such as 100° or 120° C., at the support surface (or in the sample) to release the bound water so that it may be vaporized by the microwave radiation. Thus, lossy dielectric or polar substance is removed but the sample will not be adversely affected, even if it is sensitive to scorching when heated (which could cause false analytical readings or could make a dried product unacceptable).

Another method of improving the process and protecting material being treated utilizes a particulate inert and thermally stable material of about the same particle size (in the same range) as the sample (normally Nos. 10 to 325 sieves, U.S. Sieve Series), which is mixed with the sample being treated. Various such dispersants or diluents may be employed but of these the best are considered to be quartz, sand and salt, all of which are microwave transmissive and contain little or no moisture. If the diluent does contain moisture it is preferred that it be dried before being mixed with the product to be treated and analyzed, such as low fat milk powder, coffee, detergent composition, paper or grain. Alternatively, its moisture content may be taken into account in analyses. The proportion of sample to dispersant will normally be within the range of 1:0.2 to 1:5, preferably 1:0.5 to 1:3 and more preferably 1:1 to 1:2, for best results. While use of the diluent is especially effective in conjunction with employment of the present support (and preferably with the intervening pad or mat) it also has wider application in microwave operations, and especially in analyzing and dehydrating procedures like those described herein when they are effected with microwave radiation. Thus, the volatilizable components of the material to be analyzed or heated may be driven off without causing thermal degradation of such material when the compatible and thermally stable inert dispersant, in particulate or powder form, is utilized to prevent local overheatings of sample particles.

The following examples illustrate but do not limit the invention. Unless otherwise indicated, all temperatures are in °C. and all parts are by weight.

EXAMPLE 1

27 Grams of No. 3110 RTV silicone rubber and 4 grams of Trans-Tech G-1210 ceramic garnet in powdered form are mixed together on a non-sticking surface (such as one coated with Teflon) or in a container having such a surface, until the powder is homogeneously dispersed in the matrix, after which nine drops or 0.5 gram of catalyst (RTV catalyst No. 4) are added and are mixed into the sample. A mold of desired shape and dimensions, which is circular, of a diameter of 10.5 cm. and a depth of 2.2 mm., is inverted and is pressed over the mixture until the mixture completely fills it. After an initial curing time of approximately five minutes the partially cured, disc-shaped support is removed from the mold, after which a final curing is performed in a thermal oven (although a microwave oven may also be employed) over a period of about 40 minutes at a temperature of about 115° C. When the support made is to be used in an AVC apparatus, which is equipped with a built-in balance, the progress of the final curing will be observed to make sure that no further weight loss occurs. This condition is not critical when the support is to be employed in conjunction with an MDS apparatus, in which the support is not placed on a built-in balance.

In a variation of this example eight grams of the described silicone rubber, 4 grams of the garnet powder and three drops or 0.2 gram of catalyst are employed and the disc-shaped support made is 0.7 mm. thick. In another embodiment of the invention four grams of the silicone rubber, 2 drops or 0.1 gram of catalyst and three grams of garnet powder are employed, and the support made is of the same diameter but is only 0.2 mm. thick. Such operations are also carried out to make other supports of the same disc shape but having yttrium garnet G-113, nickel ferrite TT2-111 and lithium ferrite TT2-3000 separately substituted for the aluminum doped garnet G-1210. Similarly, mixtures of two or more such ferrites and/or garnets, in equal parts, are utilized. Alternatively, instead of the silicone rubber polytetrafluoroethylene molding powder is used, in the same proportions, with the "curing" conditions being modified accordingly. Instead of these matrices other polymeric materials, such as were previously mentioned, may be used and others of the described microwave absorptives may be substituted for the spinels and garnets.

Of the products made it is generally preferable to utilize that which is the thickest (2.2 mm.) because it can be preheated and kept hot during and between tests or heatings of materials and is less likely to be damaged in use. It is noted that the limiting pad temperature will generally be below the Curie temperature of the ferrite, garnet or mixture thereof, apparently due to an equilibrium between heat dissipation by the support and heat generation by the microwave radiation absorptive material. It has been found that the temperature to which the support is raised is dependent on the Curie temperature and on the concentration of the microwave absorptive material. The rate of heating depends on the magnetization saturation of the absorptive material, the concentration thereof and the thickness of the support, and the rate of cooling depends primarily on the thickness of the support and the composition thereof.

The described supports, in flat disc form, can be made of as great a diameter as desired, even up to 30 cm., whereas even much smaller discs made of ceramic ferrites and garnets tended to become brittle, apparently due to rapid heatings and coolings, and often broke after several uses despite being very carefully handled. Such fragility was worse for the larger ceramic discs and therefore they were effectively limited in size to about 7 or 8 cm. in diameter. The present discs may be made as large as will normally be wanted and often will be in the 10 to 20 cm. diameter range.

Instead of flat disc-shaped supports the supports may be of various other suitable shapes, such as that shown in FIG. 6, or the matrix-absorptive particles mixes of this example may be employed to coat or line a vessel. For example, with TFE being used as the matrix and any of the ferrites or garnets or mixtures thereof being dispersed in it in the proportions indicated, such mix may be sprayed onto or otherwise applied to the inner surface of an evaporating dish made of TFE. Powdered TFE and absorptive particles may be pressed and "cured" onto the vessel interior, too. Also, mixtures of matrix and absorptive particles may be enclosed in a film envelope, as shown in FIG. 8.

The supports of this example are satisfactory when employed in conjunction with microwave heating apparatuses, such as those of the CEM Corporation, previously described, and specific such processes are illustrated in the following examples.

EXAMPLE 2

Using any of the circular disc supports described in Example 1, and preferably employing the first mentioned such disc in an apparatus like that shown in FIG. 3, various materials are analyzed for moisture content. In all such cases about two grams of product are spread out over the surface of a fiberglass pad of similar diameter and about 0.7 mm. thick, which is on a preheated (to about 90° C.) support. Before placing the specimen on the pad the tare weight is taken of the heated disc and the pad, and after placement of the specimen and distribution of it over the surface of the pad so that it is rather evenly distributed, the total weight is recorded, so that the weight of the specimen may be calculated by subtraction of the tare weight.

Standard tests for moisture contents of products, such as dry non-fat milk powder, which contains approximately 50% lactose and its water of hydration, which is releaseable at approximately 120° C., require oven drying at about 100° C. for four hours or toluol distillation, which takes about an hour. When microwave radiation alone is employed, for a sample which contains 3.4% of moisture by one of the standard methods, even with eight minutes drying time at 550 watts power and with a smaller sample weight (about 1.5 grams) the moisture content indicated is lower than actual (2.2% vs 3.4%). However, employing the support of this invention (120° C. type) at only 300 watts power and for a drying time of 4 to 5 minutes with a sample weight of three grams, a 3.4% moisture analysis is obtained. Furthermore, similar results are obtainable when the power is higher initially, e.g., 550 watts, for about the first two minutes and then is lowered to 300 watts for another minute or two.

Similar results are also obtained in analyzing coffee, which also contains a significant percentage of bound water, the analysis for which by conventional microwave techniques has often been unsuccessful. That is also the case when animal feeds are analyzed, in which the moisture content is higher, often about 8%, and in which the protein contains bound water. Thus, with twice the amount of sample and half the drying time, utilizing the same microwave power, such products analyze 8% moisture, compared to an incorrect low reading of 6.2% moisture by conventional microwave analysis with the AVC-80 apparatus.

The process of this invention is also useful for heating materials containing volatiles other than moisture. Because of the thermal heating effect, in conjunction with microwave heating, such non-polar volatiles are also removable whereas such would not be removed by microwave heating alone unless a polar material or a lossy dielectric was also present to absorb the microwave radiation and convert it to heat.

EXAMPLE 3

The processes described in Example 2 are utilized in conjunction with the apparatus of FIG. 1 (MDS-81) to dry materials containing minor proportions of moisture and/or volatiles. The flat disc or a plurality of such discs, preferably four thereof, each with a pad on it holding a sample to be dehydrated, preferably of about the same weight and of the same material, will be placed on the turntable and will be subjected to approximately the same power for the same time for the same sample weights of such materials as was employed in Example 2. Thus, if four specimens are employed instead of one, the total microwave radiation will be four times that applied in Example 2. The results obtained are like those reported in Example 2. The apparatus of this example, which allows the heating and drying of plurality of samples, is more efficient in this respect than the AVC apparatus but the latter apparatus has the advantage of automatically weighing the sample so that it does not have to be removed from the microwave apparatus and separately weighed.

EXAMPLE 4

Using the MDS-81 apparatus for the drying of non-fat milk powder (either whole milk or whey) Programs 1, 2 and 3 are set as follows: 1–100% power for 1.5 minutes; 2–75% power for five minutes; and 3–100% power for 15 minutes. Two supports of the first type described in Example 1, both of which are circular discs, are placed on the turntable on top of round fiberglass pads and are preheated for 15 minutes in accordance with Program 3 so that the supports and pads come to constant temperature, at about 90° C. Two Petri dishes are each lined with a fiberglass pad. The first is weighed and ten grams of salt are added to it so that the total weight on the balance will be in the range of about 22.8 to 23.1 grams, the tare weight. The tare weight is stored by depressing Button No. 1 (for Sample No. 1) and Tw on the HP calculator. Approximately seven grams of milk powder are added to the Petri dish, the sample is removed from the balance pan and the salt and milk powder are mixed. A slight color change indicates a thoroughly mixed sample. Then the sample is returned to the balance pan and the initial weight is stored, depressing No. 1 and Wi. A second sample is then prepared in the same manner. The MDS apparatus will be preheating (Program 3) while the samples are being prepared. When they are ready for testing the MDS is then stopped by depressing STOP. The instrument will automatically reset to Program 1, the samples will be placed on the preheated supports, and their locations are recorded. The test will then be started by pressing RUN. The display then reads 100% power, 1.5 minutes in Program 1. After ending of Program 1 the display next reads 75% power, five minutes in Program 2. After Program 2 has counted down to 0 time two beeps will be sounded to indicate that the test is over. At that time Sample 1 will be removed from the apparatus and weighed (after stabilization) and then the same operation will be repeated for Sample 2. Next Calculate Buttons C-1 and C-2 will be pressed in that order and the calculator then prints out the sample numbers, actual initial weights, tare weights, final weights of the samples and moisture contents. After completion of the tests the samples are then checked for any signs of burning. None will normally be noted and so the start button may be pressed to begin the preheat in Program 3. After wiping off any excess powder from the Petri dish two more samples may be run in the same manner.

Using the support described first in Example 1 and a sample of non-fat milk powder having a moisture content of about 3%, the sample is analyzed for moisture content by the described method and accurate results, essentially the same as those obtained by conventional analytical methods, are obtained. Such results are also obtained when flour, animal feeds, wood, synthetic organic detergents (built with hydrated inorganic salts, such as polyphosphates), and other relatively low moisture content products (and some of higher moistures) are analyzed.

When the support used is one designed to give a controlled temperature of 120° C. and the program is changed so that the second stage thereof is for five minutes at 50% of full power, the run is repeated, using seven samples of the milk powder, two at a time, plus one. Following are the results:

| Run No. | Wi | Moisture |
| --- | --- | --- |
| 1 | 6.941 | 2.94% |
| 2 | 7.938 | 3.01% |
| 3 | 6.931 | 3.03% |
| 4 | 6.788 | 3.02% |
| 5 | 7.153 | 2.96% |
| 6 | 7.887 | 2.99% |
| 7 | 7.058 | 2.93% |

The standard analysis of the same material indicated 3.0% of moisture and, of course, that test took much more time. Note that the standard deviation is only 0.04% from the average of 2.98%.

The same test, run on the AVC-80 apparatus, also results in similarly accurate determinations of moisture for milk powder of the type described, for whey, wheat, animal feeds, woods, detergents and inorganic salts. Such results are obtainable for many of the mentioned materials without the presence of the diluting salt (or sand or quartz, which may be substituted, too) especially for those materials, such as wood and detergents, which do not tend to scorch during such a test. Also, with the AVC-type automatic weighing device usually the amount of sample will be smaller, generally being about 3 grams. The heating time will be about the same, normally being about five to eight minutes, and the power may be full for the whole test. Of course, if any charring of the sample is detected the power should be reduced and often it is also desirable to cut the power delivered when a loss of weight of more than 0.1 gram per minute is observed. When the same milk powder that was analyzed by the MDS-81 apparatus is analyzed by the described method with the AVC-80, the moisture content is found to be 3.0%.

The employment of the dispersant salt, sand or quartz, or equivalent material to prevent scorching of sensitive materials being analyzed, as for moisture content, is also useful for microwave analytical processes when the support is not employed or when a support used does not have a Curie temperature, so that the heating of the sample being analyzed is not "controlled", as it is in the present processes. However, because most materials being analyzed do not heat up due to exposure to microwave radiation once the moisture is almost removed from them (or at least their rate of heating slows down noticeably), the danger of scorching is less. Nevertheless, the diluent or dispersant, such as salt powder, may be and is used with milk powder and other materials named previously in this example to help to spread the heat generated, reduce any possible scorching or adverse thermal reactions, and produce a more accurate analysis. The dispersant helps to hold some heat and thereby aids in drying the sample after microwave absorption is slowed or halted. However, the analytical results obtained are not as accurate as those wherein the same apparatus conditions are employed (as in this example) with the use of the support of this invention.

EXAMPLE 5

Utilizing the MDS-81 apparatus, at 80% of full power, five different samples of tobacco are taken from the same container and are heated by the apparatus of this invention, including a support of the type described in Example 1, but thinner and of larger diameter to accommodate the material being tested. Instead of employing four supports, as in Example 3, only one support is utilized, which is about 1 mm. thick and of a diameter equal to that of the surface of the turntable, or about 30 cm. It has been found that such a larger support is desirable for testing the larger samples, e.g., 20 grams or more, of tobacco and of other low bulk density materials to be analyzed for moisture (and volatiles). The thinner support even better conforms to the surface of the turntable and is adequate for the production of sufficient thermal heat to be conveyed to the sample. The turntable surface is of suitable Teflon coated glass screening, normally of a size like those screens of a mesh size in the No. 10 to 50 range, U.S. Sieve Series, although other mesh sizes can also be operative.

The finely divided tobacco sample is spread over the surface of the fiberglass pad, of the type previously described, which has a diameter approximately that of the support. The apparatus is turned on and kept at about 80% of full power for appoximately five minutes, after which the glass pad, with the tobacco on it, is allowed to cool, and is weighed. The moisture (or volatiles content) is found and recorded, after which the test is repeated four more times, to verify the accuracy of the determination. For sample weights of 21.636 g., 20.503 g., 23.701 g. 19.667 g., and 21.662 g., the moisture (including volatiles) analyses were 13.37%, 13.48%, 13.63%, 13.38%, and 13.24%, averaging 13.42%. Another sample of the same tobacco was taken and was analyzed by the conventional method of drying for two hours in an oven and by this method the moisture content was found to be 13.69%. Thus, even the lowest moisture analysis by the method of the present invention, done in only five minutes, was only 0.45% lower than that obtained by the conventional two-hour moisture determination. Previously, microwave apparatus moisture determinations of tobacco have been found to be inacurrate, often being up to about 2% lower than actual moisture content, as determined by oven drying.

The analytical procedure described above is of great importance to the tobacco industry, especially for the manufacturing of cigarettes and other tobacco products, wherein moisture control is very important (because incorrect moisture can adversely affect the characteristics of the cigarettes made and can interfere with the operation of the high speed manufacturing equipment). With the present apparatus the actual moisture of the tobacco being employed can be checked very quickly, and off-specification tobacco can be prevented from entering the manufacturing line. Thus, this apparatus allows much better operational and quality control in the tobacco industry.

In the foregoing examples various other embodiments of the invention may be substituted and the same types of results are obtainable. Thus, any of the various ferrites and garnets described in the Trans-Tech publications may be employed and they may be used in mixtures in the supports. However, often yttrium garnets having Curie temperatures in the 85° to 280° C. range will be substituted preferably and nickel ferrites of Curie temperatures in the 120° to 500° C. range may also be preferred. Instead of silicones and TFE, FEP and others of the mentioned polymers and elastomers may be used too, and good results are obtainable. Proportions given in the example may be changed ±10, 20 and 30 percent without making the processes and products inoperative. Heating times, power levels, wavelengths and particle sizes may also be changed so long as they remain in the ranges recited (if ranges are set herein), and good results will be obtained. Although the spinels and garnets are highly preferable microwave absorptives and heaters for the temperature limited supports of this invention other absorptives may be substituted for them, either in whole or in part, but preferably only partly, such as ferromagnetic and ferroelectric materials. The ferrites are ferrimagnetic. Among the ferromagnetics are the Heusler alloys of manganese, tin and copper, or manganese, aluminum and copper, and among the ferroelectrics are the zirconates of lead and barium, and the titanates of lead, barium and strontium. Such materials will be used in the same range of particle sizes and at the same concentrations in the same matrices as previously noted.

In another modification of the foregoing examples the silicone rubber-absorptive mixture is cured to sheet form and the various shapes of supports are cut from the sheet as needed. Thus, they can be made to order on site for many of different apparatuses and applications.

Various advantages of the invention have been mentioned in this specification and have been illustrated in the examples. These will be summarized here and a few others will be recited. First, it is evident that the present invention allows quick and accurate analyses, dryings and heatings of a wide variety of materials, sensitive and insensitive to heat. Employment of the support allows thermal heating of a sample after most moisture has been removed from it. For apparatuses like the AVC microwave heater and analyzer the microwave heating of the support allows continuing weighings of the sample without the interference of connections to a heater, such as might be used otherwise if thermal heating was to be employed. The supports made do not crack or deteriorate on use, as do ceramic supports. Because the supports with a continuous matrix or other diluent extend the microwave absorptive material, they may be made of various heating characteristics, and the cost of the heating supports may be decreased. Also, the supports may be reworked and incorporated in other matrices if particular shapes made become obsolescent. The supports may be made in sheet or strip form of almost unlimited sizes and may be cut to desired shape. Several supports may be used together to vary the heating capacity and heating effects, as by placing them one atop the other. They may be cut to patterns and then stitched or otherwise held together to form special shapes. Because the supports are flexible when the matrix material is an elastomer, such as silicone rubber, they adhere to surfaces on which they are placed, sufficiently so that they can be used with a turntable type of microwave apparatus and will not slide. However, it is often desirable to place them on a fiberglass pad to prevent any movement, especially when the matrix is of TFE or other relatively slippery polymer. The apparatuses incorporating the mentioned supports are capable of analyzing materials for moisture and other volatiles that may be difficultly removable by means of microwave radiation alone. Whereas before analyses of such products were inaccurate, now they can be run fast and the results will be as good as those obtained by the longer, more labor-intensive methods. A new field of analytical operations has been opened. Not only is the new apparatus more efficient and cost-saving, it also allows rapid analyses of products as they are being manufactured, so that moisture and volatiles contents thereof may be controlled and so that the materials being made may be kept on specification. Otherwise, an hour's production may have to be scrapped or a material that is too high in solids content may be produced, which can cause considerable financial losses over a period of time. The processes of this invention are trouble-free and simple. They may be carried out by unskilled personnel instead of trained chemists or laboratory technicians. Thus, they are especially useful in manufacturing facilities that are located at a distance from central laboratories. They allow performance of an important quality control test without the need for a quality control laboratory. Furthermore, because of the controllability of the heating of the sample being tested, materials that previously might not have been analyzable by methods which used heat to drive off volatiles, because of sensitivity to overheating, can now be analyzed without fear of decomposition.

The invention has been described with respect to examples and illustrations thereof but it is not to be limited to these because one of skill in the art with the present specification and drawing before him will be able to utilize substitutes and equivalents without departing from the invention.

What is claimed is:

1. A process for/analyzing a thermally sensitive material for its content of volatilizable components without degrading the material, which comprises supporting the material to be analyzed, which includes lossy and non-lossy volatilizable component(s), by means of a support which comprises 40 to 95% of a matrix material which is transmissive of microwave radiation, 5% to 60% of a microwave absorptive material dispersed in such matrix material, which microwave absorptive material has a Curie temperature in the range of 85° to 650° C., above which it becomes microwave transmissive, so as thereby to prevent excessive heating of the support and the material to be analyzed, which matrix material is stable and form retaining at the Curie temparature of the dispersed material, and directing microwave radiation onto the material to be analyzed and onto the support for such material so as directly to heat the material when it contains lossy volatilizable component(s) and indirectly to heat such material by heating the support when the material to be analyzed no longer contains any lossy component(s), which support heats the material to a temperature no higher than the Curie temperature of the dispersed microwave absorptive material in the matrix of the support, at which temperature the material being analyzed is not degraded, and applying sufficient microwave radiation to bring the microwave absorptive material of the support to its Curie temperature.

2. A process according to claim 1 wherein the support comprises a body of matrix material which is transmissive of microwave radiation, with a coating thereon of a microwave absorptive material dispersed in such matrix material.

3. A process according to claim 2 wherein the material to be controllably heated and analyzed is a material containing moisture which is removable by microwave heating and which is removed by such heating during the process, which material contains additional moisture which resists removal by microwave heating and is removable by indirect microwave heating, whereby heat is transmitted to it from the microwave heated support through the intermediate fiberglass mat, and which additional moisture is removed by such indirect heating during the process.

4. A process according to claim 3 wherein the material to be controllably heated and analyzed is in particulate form, of particle sizes substantially all of which are in the range of Nos. 10 to 325 sieves, U.S. Sieve Series, and is dispersed in a particulate inert and thermally stable material, the particles of which are substantially all in the range of Nos. 10 to 325 sieve, U.S. Sieve Series, with the proportion of material to be controllably heated and analyzed to the dispersant being within the range of 1:0.2 to 1:5.

5. A process according to claim 2 wherein the matrix material is polytetrafluoroethylene, the Curie temperature of the microwave absorptive material is in the range of 105° to 500° C., the microwave absorptive material is in finely divided particulate form, the percentages of matrix material and microwave absorptive material in the coating are from about 40 to 95% and 5 to 60%, respectively, and the support is in the form of an evaporating dish, the body portion of which is of a thickness in the range of 0.5 to 3 mm. and the coating of which is of a thickness in the range of 0.5 to 3 mm.

6. A process according to claim 1 wherein the support is in the form of a supporting body in which the matrix material is a continuous phase and the microwave absorptive material is in finely divided particulate form, substantially evenly dispersed throughout the matrix material, and the microwave absorptive material is selected from the group consisting of ferrites, garnets and mixtures thereof.

7. A process according to claim 6 wherein the thermally sensitive material to be controllably heated and analyzed contains a lossy dielectric, which makes it microwave absorptive, at least a major proportion of which lossy dielectric is removed by direct microwave heating of the material, and the material is supported directly by an intermediate fiberglass mat which rests on the support.

8. A process according to claim 1 wherein the material to be controllably heated and analyzed is in particulate form, of particle sizes substantially in the range of Nos. 10 to 325 sieves, U.S. Sieve Series, and is dispersed in a particulate, inert and thermally stable material, the particles of which are substantially in the range of Nos. 10 to 325 sieves, with the proportion of material to be analyzed to the dispersant being within the range of 1:0.2 to 1:5, by weight.

9. A process according to claim 8 wherein the material being analyzed is milk powder, the volatilizable component of which is water, the dispersant for the milk powder is selected from the group consisting of salt, sand and quartz, and the proportion of milk powder to dispersant for it is in the range of 1:0.5 to 1:3.

10. A process according to claim 9 wherein the milk powder contains about equal proportions of protein and lactose, and 2 to 5% of water, the dispersant for the milk powder is salt, the microwave absorptive material is selected from the group consisting of ferrites, garnets and mixtures thereof, the matrix material is selected from the group consisting of silicone rubbers and polyfluoroalkylene polymers, and the sample of milk powder being analyzed is on an intermediate fiberglass mat which rests on and is in contact with the support.

* * * * *

UNITED STATES PATENT AND TRADEMARK OFFICE
CERTIFICATE OF CORRECTION

PATENT NO. : 4,681,996
DATED : July 21, 1987
INVENTOR(S) : Michael J. Collins et al.

It is certified that error appears in the above-identified patent and that said Letters Patent is hereby corrected as shown below:

The term of this patent subsequent to January 28, 2003 has been disclaimed.

Signed and Sealed this

Eighth Day of September, 1987

Attest:

DONALD J. QUIGG

*Attesting Officer*   *Commissioner of Patents and Trademarks*